(12) United States Patent
Kremminger et al.

(10) Patent No.: US 6,787,649 B2
(45) Date of Patent: Sep. 7, 2004

(54) CEPHALOSPORIN INTERMEDIATES

(75) Inventors: Peter Kremminger, Kundl (AT);
Johannes Ludescher, Breitenbach (AT); Siegfried Wolf, Brixlegg (AT)

(73) Assignee: Sandoz GmbH, Kundl (AT)

( * ) Notice: Subject to any disclaimer, the term of this patent is extended or adjusted under 35 U.S.C. 154(b) by 0 days.

(21) Appl. No.: 10/258,624

(22) PCT Filed: Apr. 26, 2001

(86) PCT No.: PCT/EP01/04735

§ 371 (c)(1),
(2), (4) Date: Feb. 12, 2003

(87) PCT Pub. No.: WO01/83491

PCT Pub. Date: Nov. 8, 2001

(65) Prior Publication Data

US 2003/0153748 A1 Aug. 14, 2003

(30) Foreign Application Priority Data

Apr. 28, 2000 (GB) ............................................ 00104752

(51) Int. Cl.⁷ ....................... C07D 501/36; C07D 277/46
(52) U.S. Cl. ........................................ 540/227; 548/195
(58) Field of Search ........................................ 540/227

(56) References Cited

U.S. PATENT DOCUMENTS

| | | | | |
|---|---|---|---|---|
| 4,394,384 A | * | 7/1983 | Takaya et al. | 540/227 |
| 4,487,767 A | * | 12/1984 | Takaya et al. | 540/227 |
| 5,625,058 A | | 4/1997 | Pessa et al. | |

FOREIGN PATENT DOCUMENTS

| | | |
|---|---|---|
| EP | 128 029 | 12/1984 |
| WO | WO 96/17850 | 6/1996 |

\* cited by examiner

*Primary Examiner*—Mark L. Berch
(74) *Attorney, Agent, or Firm*—John D. Thallemer; Diane E. Furman

(57) ABSTRACT

A process which comprises
(i) acylating a compound of formula II

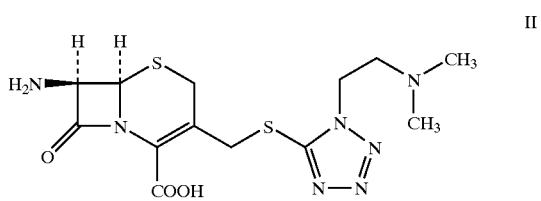

with a compound of formula IV

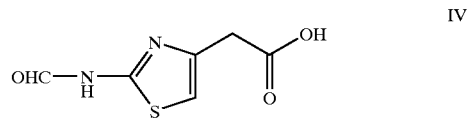

to obtain a compound of formula I

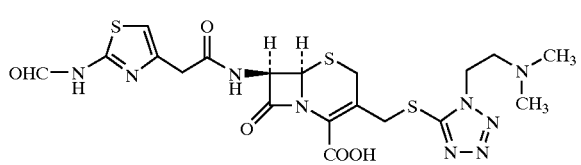

and
(ii) deformylating said compound of formula I to obtain a compound of formula III

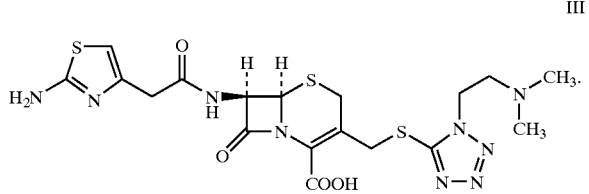

9 Claims, No Drawings

CEPHALOSPORIN INTERMEDIATES

The present invention relates to β-lactams, more specifically to cephalosporins e.g. cefotiam, such as of formula

III

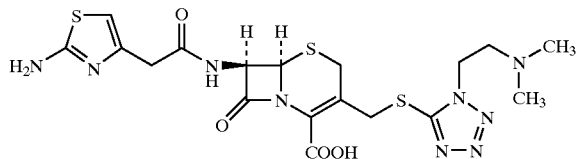

see e.g. Merck, 12$^{th}$ edition, item 1985.

An oral form of cefotiam for administration may contain cefotiam in the form of cefotiam hexetil, i.e. (6R,7R)-[1-(cyclohexyloxycarbonyloxy)ethyl]-7-[2-(2-amino-1,3-thiazol-4-yl)acetamido]-3-[[1-(2-dimethylaminoethyl)-1H-tetrazol-5-yl]thiomethyl]-8-oxo-5-thia-1-azabicyclo[4.2.0]oct-2-ene-2-carboxylate; e.g. in the form of a dihydrochloride. A parenteral form may e.g. contain cefotiam in the form of a dihydrochloride.

Cefotiam, e.g. in the form of a dihydrochloride, which may be used as an intermediate in the production of cefotiam hexetil, may e.g. be produced by acylation of the amine group in (6R,7R) 7-amino-3-[[1-(2-dimethylaminoethyl)-1H-tetrazol-5-yl]thiomethyl]-8-oxo-5thia-1-azabicyclo[4.2.0]oct-2-ene-2-carboxylic acid (7-ACMT) of formula

II

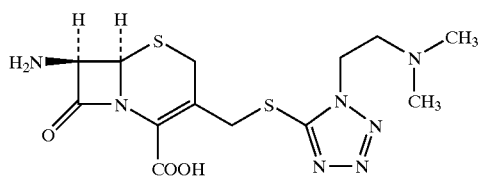

with 4-chloro-3-oxobutyryl chloride, followed by ring formation with thio urea to obtain the aminothiazolyl ring in the side chain attached to the amine group in position 7 of the ring structure.

We have found surprisingly a novel and simple process for the production of cefotiam.

In one aspect the present invention provides a process for the production of cefotiam, e.g. a compound of formula III, comprising (i) acylating a compound of formula II; e.g. in the form of a salt, e.g. a salt with an halogenic acid, such as hydrochlorid acid, hydrobromic acid; e.g. a mono- or dihydrochloride; or a mono- or dihydrobromide; or a salt with tetrahydroboric acid; with a compound of formula

IV

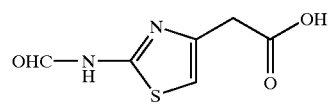

in an activated form; to obtain a compound of formula

I

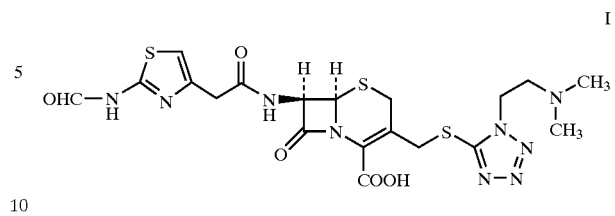

e.g. in free form or in the form of a salt, e.g. an alkali metal salt, or a salt with an amidine, a guanidine, ammonia or an amine; preferably in the form of a salt with an amine; and (ii) deformylating a compound of formula I to obtain a compound of formula III, e.g. in the form of a hydrochloride, such as a dihydrochloride.

Alkali includes e.g. sodium, potassium. An amidine includes e.g. DBU (1,8-diazabicyclo(5,4,0)undec-7-ene) and DBN (1,5-diazabicyclo(4,3,0)non-5-ene). A guanidine includes tetramethylguanidine. An amine includes an amine of formula $NR_1R_2R_3$, wherein $R_1$, $R_2$, and $R_3$ independently of each other are hydrogen, alkyl, or aryl; or $R_2$ and $R_3$ together with the nitrogen atom to which they are attached denote heterocyclyl and $R_1$ is hydrogen, alkyl, aryl or represents an additional bond to form a double bond to $R_2$ or to $R_3$. Preferably an amine includes e.g. tertiary amines, e.g. aliphatic, such as triethylamine, tributylamine, ethyldi-isopropylamine; secondary amines, such as dibutylamine and primary amines, e.g. tert. octylamine (2,2,4-trimethylpentaneamine). If $R_2$ and $R_3$ together with the nitrogen atom to which they are attached are heterocyclyl, an amine includes cyclic unsaturated or saturated amines, such as N-methylpyrrolidine, N-ethylpiperidine, pyridine, chinoline. An amine may be unsubstituted or substituted; substituents include e.g. halogen, alkyl, e.g. $(C_{1-4})$alkyl; nitro, alkoxy, e.g. $(C_{1-4})$alkoxy. Preferably an amine is tributylamine. If not otherwise defined herein, alkyl includes $(C_{1-8})$alkyl, such as $(C_{1-4})$alkyl; and aryl includes phenyl, naphthyl, preferably phenyl. Heterocyclyl includes a saturated or unsaturated ring system; e.g. aliphatic or aromatic; e.g. having 5 to 7 ring members; e.g. being anelled to a further ring (system); e.g. of 4 to 12 ring members. Heterocyclyl may contain one or more, e.g. 1 to 4 hetero atoms; e.g. selected from O, S, N.

A solvent or a solvent system includes one single solvent and a mixture of two or more individual solvents.

A compound of formula I, e.g. in free form and in the form of a salt, is new.

In another aspect the present invention provides a compound of formula I, e.g. in free form or in the form of a salt; e.g. an alkali metal salt, or a salt with an amidine, a guanidine, ammonia or an amine, such as in the form of a salt with tributylamine, e.g. tri-n-butylamine.

In another aspect the present invention provides a process for the production of a compound of formula III, comprising deformylating a compound of formula I, e.g. in free form or in the form of a salt; e.g. an alkali metal salt, or a salt with an amidine, a guanidine, ammonia or an amine; to obtain a compound of formula III, e.g. in free form or in the form of a salt; e.g. a hydrochloride, such as a dihydrochloride; and isolating a compound of formula III.

A compound of formula I may e.g. be obtained by reaction of a compound of formula IV in an activated form, with a compound of formula II.

In another aspect the present invention provides a process for the production of a compound of formula I, comprising reacting a compound of formula IV in an activated form with a compound of formula II; and isolation of a compound of formula I.

A process according to the present invention may be carried out as follows:

A compound of formula II, in free form or in the form of an acid addition salt; e.g. an acid addition salt with hydrochloric acid, tetrafluoroboric acid; is dissolved in a solvent; e.g. an organic solvent; in the presence of a base; e.g. including ammonia, amines, amidines, guanidines; and is reacted with a compound of formula IV in an activated form. A compound of formula I is obtained in the form of a salt with an amidine, e.g. if an amidine is used as a base;
a guanidine, e.g. if a guanidine is used as a base;
ammonia, e.g. if ammonia is used as a base;
an amine, e.g. if an amine is used as a base.

A compound of formula I, e.g. in the form of a salt, may be obtained in crystalline form. E.g. a compound of formula II in a solvent system is treated with a base and a compound of formula IV in an activated form; and a compound of formula I in the form of a salt may precipitate; e.g. on addition of an anti-solvent to the reaction mixture. An anti-solvent includes organic solvent which lowers the solubility product of a compound of formula I in a solvent on addition to said solvent.

A compound of formula I in free form may be obtained by treatment of a compound of formula I in the form of a salt, e.g. a salt with an amidine, a guanidine, ammonia or or an amine; with an acid; e.g. including a strong acid, e.g. a mineralic acid, such as hydrochloric acid, hydrobromic acid, hydrosulphuric acid; or mixtures of individual acids; e.g. in the presence of organic solvent and optionally in the presence of water.

A compound of formula I in the form of an alkali metal salt, e.g. including sodium and potassium, may be obtained, e.g. by treating a compound of formula I in free form with an alkali source, e.g. an alkali salt, e.g. a sodium or potassium salt, such as an alkali metal salt of a carboxylic acid, e.g. an alkali acetate, hexanoate; e.g. in the presence of an alcohol.

A solvent system includes e.g. halogenated, such as chlorinated, hydrocarbons, e.g. dichloromethane; nitriles, e.g. acetonitrile; ketones, e.g. acetone, methylethylketone, methylisobutylketone; ethers, e.g. tetrahydrofurane; esters, e.g. ($C_{1-3}$)carboxylic acid ($C_{1-4}$)esters; and mixtures of individual solvent, e.g. as described above. Anti-solvent includes solvent (system) as described above; water and alcohols, e.g. including($C_{1-4}$)alcohols.

In a preferred process of the present invention tributylamine, e.g. tri-n-butylamine, is used as a base; a compound of formula II is preferably in the form of a salt with hydrochloric acid or tetrafluoroboric acid; a preferred solvent includes acetonitrile.

The amount of the base used is not ciritcal; per equivalent of a compound of formula II one equivalent of a base may be used; or an higher amount of a base; e.g. 2 to 3 equivalents.

An additional amount of a base may preferably be used, e.g. 2 to 8 equivalents, e.g.

in the case that a compound of formula II is used in the form of an acid addition salt, e.g. a corresponding additional amount which is necessary to neutralize the acid which is set free during reaction with a compound of formula IV in an activated form;

in the case that a compound of formula IV in activated form is a carboxylic acid halogenide, e.g. chloride, e.g. a corresponding additional amount which is necessary to neutralize the halogen acid set free during reaction with a compound of formula II;

in the case that a compound of formula IV in an activated form is in the form of a salt, e.g. in the form of an acid addition salt; e.g. a corresponding additional amount which is necessary to neutralize the acid which is set free during reaction with a compound of formula II.

A compound of formula IV in an activated form includes a reactive form of a compound of formula IV, e.g. carboxylic acid halogenides, e.g. chlorides, bormides; carboxylic acid esters, e.g. carboxylic acid S-mercaptobenzthiazolyl esters, hydroxybenztriazolyl esters. Activation of a compound of formula IV may be performed via Vilsmeier activation, e.g. in situ. A compound of formula IV is preferably an acid chloride, e.g. in free form or in the form of a salt, e.g. an acid addition salt, such as a salt with hydrochloric acid, hydrobromic acid; more preferably a compound of formula IV is a compound of formula

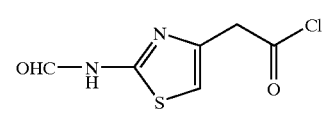

V e.g. in free form or in the form of a salt, e.g. a salt with hydrochloric acid, hydrobromic acid; preferably hydrochloric acid.

A compound of formula V in isolated form is new.

In another aspect the present invention provides an isolated compound of formula V, e.g. in free form or in the form of a salt; e.g. a salt with hydrochloric acid, hydrobromic acid; preferably hydrochloric acid.

A compound of formula V may be obtained by reaction of a compound of formula IV with $PCl_5$ in a solvent, e.g. a solvent which is inert, under the reaction conditions, such as an halogenated, e.g. chlorinated, hydrocarbon, e.g. dichloromethane. A compound of formula V may precipitate and may be isolated, e.g. and dried, e.g. according to a method as conventional.

A compound of formula III, e.g. in free form, or in the form of a salt; e.g. a hydrochloride, such as a dihydrochloride; and/or in the form of a solvate, such as a hydrate, may be obtained as follows:

A compound of formula I may be deformylated by acid treatment, e.g. according to a method as conventional, e.g. preferably as follows:

A compound of formula I in an aqueous, acidic medium, e.g. aqueous hydrochloric acid; may be kept for serveral hours, e.g. 2 to 6 hours, at temperatures of 20° C. to 40° C., such as around 30° C. A compound of formula III; e.g. in the form of a salt; e.g. a hydrochloride, such as a dihydrochloride; and/or in the form of a solvate; may be obtained and may be isolated; e.g. precipitated; e.g. according to a method as conventional; e.g. by addition of an anti-solvent, e.g. a ketone, such as acetone.

A process according to the present invention is simple to carry out and may be used on technical scale. The use of an intermediate of formula I, which may surprisingly be crystalline, may provide a high purification effect for cefotiam. Cefotiam produced according to the present invention may be used in the production of cefotiam hexeol, see. E.g. Merck, $12^{th}$ edition, item 1985.

In another aspect the present invention provides the use of a compound of formula I; or of a compound of formula III produced according to the present invention; in the production of (6R,7R)-[1-(cyclohexyloxycarbonyloxy)ethyl]-7-[2-(2-amino-1,3-thiazol-4-yl)acetamido]-3[[1-(2-dimethylaminoethyl)-1H-tetrazol-5-yl]thiomethyl]-8-oxo-5-thia-1-azabicyclo [4.2.0]oct-2-ene-2-carboxylate (cefotiam hexetil);

e.g. either by converting a compound of formula III, in free form or in the form of a salt, into cefotiam hexetil; e.g. by esterification of the carboxylic group in position 4 of the ring structure in a compound of formula III; e.g. according to a method as converitional; and isolating cefotiam hexetil; e.g. in free form or in the form of a hydrochloride, e.g. a dihydrochloride; e.g. according to a method as conventional;

or by converting a compound of formula I, in free form or in the form of a salt, into (6R,7R)-[1-(cyclohexyloxycarbonyloxy)ethyl]-7-[2-(2-formylamino-1,3-thiazol-4-yl)acetamido]-3-[[1-(2-dimethylaminoethyl)-1H-tetrazol-5-yl]thiomethyl]-8-oxo-5-thia-1-azabicyclo[4.2.0]oct-2-ene-2-carboxylate (N-formyl cefotiam hexetil); e.g. by esterification of the carboxylic group in position 4 of the ring structure in a compound of formula 1; e.g. according to a method as conventional; deformylating N-formyl cefotiam hexetil and isolating cefotiam hexetil; e.g. according to a method as conventional. N-formyl cefotiam hexetil, e.g. in the form of a salt and/or in the form of a solvent is new.

In another aspect the present invention provides the compound (6R,7R)-[1-(cyclohexyloxycarbonyloxy)ethyl]-7-[2-(2-formylamino-1,3-thiazol-4-yl)acetamido]-3-[[1-(2-dimethylaminoethyl)-1H-tetrazol-5-yl]thiomethyl]-8-oxo-5-thia-1-azabicyclo[4.2.0]oct-2-ene-2-carboxylate.

Any compound described herein in free form may be converted into a corresponding compound in the form of a salt; and vice versa. Any compound in free form or in salt form and in the form of a solvate may be converted into a corresponding compound in free form or in the form of a salt in unsolvated form; and vice versa.

In the following examples all degrees are given in degree Celsius.

The following abbreviations are used:
N-Formylcefotiam: A compound of formula I
ACMT: A compound of formula II

EXAMPLE 1

N-Formylcefotiam in the form of a salt with tri-n-butylamine 19.74 g of 7-amino-3-((1-(2-dimethylaminoethyl)-1H-tetrazol-5-yl)-thiomethyl-3-cephem-4-carboxylic acid in the form of a tetrahydroboric acid salt (content: 78.1% of free ACMT=0.040 mol) suspended in 100 ml of acetonitrile, are cooled to ca. −10°, treated with 42.08 ml (0.177 mol) of tri-n-butylamine and the mixture obtained is stirred. The solution obtained is cooled to ca. −40° and treated with a cooled suspension of 10.61 g (0.044 mol) of 2-formylaminothiazolyl acetylchloride in the form of a hydrochloride in 100 ml of acetonitrile. The mixture obtained is stirred for ca. 80 minutes at ca. −40°, and warmed up to ca. −20°. A crystal suspension is obtained, the crystals are filtrated off and dried.

23.87 g of N-formylcefotiam in the form of a salt with tri-n-butylamine in crystalline form are obtained. Fp: 130° C. (decomposition)

¹H-NMR(DMSO-d6): 0.88 (t, 9H, J=7.2 Hz), 1.28 (m, 6H), 1.55 (m, 6H), 2.15 (s, 6H), 2.69 (t, 2H, J=6.1 Hz), 2.85 (m, 6H), 3.44 & 3.58 (ABq, 2H, J=17.6 Hz), 3.59 (s, 2H), 4.29 & 4.30 (ABq, 2H, J=14.5 Hz), 4.36 (t, 2H, J=6.0 Hz), 4.97 (d, 1H, J=4.8 Hz), 5.55 (dd, 1H, J=4.8 & 8.4 Hz), 6.94 (s, 1H), 8.44 (s, 1H), 8.91 (d, 1H, J=8.4 Hz)

EXAMPLE 2

Cefotiam in the Form of a Dihydrochloride 6 ml of water and 4 ml of HCl (37%) are mixed and 7.14 g of N-formylcefotiam in the form of a salt with tributylamine, obtainable according to Example 1, are added in portions. The mixture obtained is warmed to 30° and kept for ca. 4.5 hours at that temperature. The warming is terminated and 6 ml of water and 100 ml of acetone are added to the mixture obtained. Further acetone is added and crystallisation occurs. The crystals obtained are filtrated off and dried.

5.34 g of cefotiam in the form of a dihydrochloride are obtained.

EXAMPLE 3

2-(2-Formylaminothiazolyl)acetic Acid Chloride in the Form of a Hydrochloride 200 g 2(2-aminothiazolyl)acetic acid in 2500 ml of dichloromethane, cooled to −200 are treated in portions with 246.4 g of PCl₅ whilst stirring. A precipitate obtained is filtrated off and dried. 232.9 g of 2-(2-formylaminothiazolyl) acetic acid chloride in the form of a hydrochloride are obtained.

Content (HPLC in free form of a methyl ester): 96.2%; Chloride-content: 28.2% (theory: 29.4%); Fp: Decomposition from 120°

What is claimed is:

1. (6R,7R)-[1-(cyclohexyloxycarbonyloxy)ethyl]-7-[2-(2-formylamino-1,3-thiazol-4-yl)acetamido]-3-[[1-(2-dimethlaminoethyl)-1H-tetrazol-5-yl]thiomethyl]-8-oxo-5-thia-1-azabicyclo[4.2.0]oct-2-ene-2-carboxylate.

2. A process which comprises (i) acylating a compound of formula II

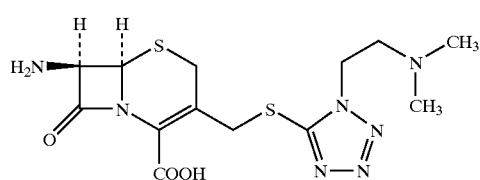

or a salt thereof with a compound of formula IV

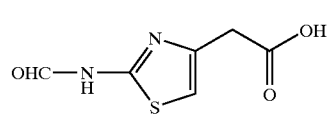

in an activated form; to obtain a compound of formula I

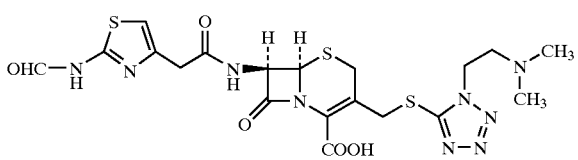

or a salt thereof, and (ii) deformylating said compound of formula I or a salt thereof to obtain a compound of formula III:

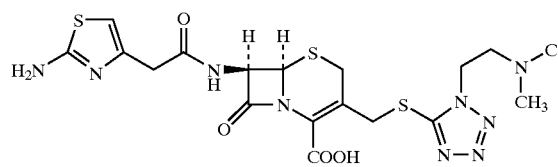

or a salt thereof.

3. A process which comprises
(i) deformylating a compound of formula I

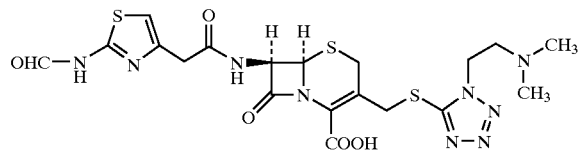

or a salt thereof to obtain a compound of formula III

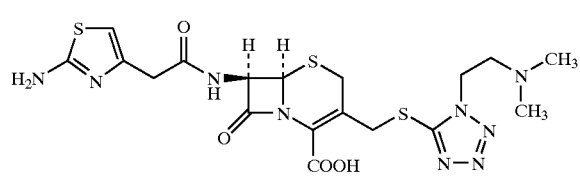

or a salt thereof
and (ii) isolating said compound of formula III or a salt thereof.

4. A process of claim 2, wherein the compound of formula III is obtained in the form of a hydrochloride salt.

5. A process of claim 4, wherein the compound of formula III is obtained in the form of a dihydrochloride salt.

6. A compound of formula I

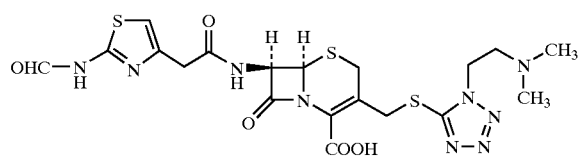

or a salt thereof.

7. A tri-n-butylamine salt of a compound of claim 6.

8. A process which comprises
(i) acylating a compound of formula II

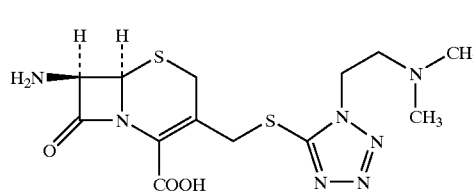

or a salt thereof with a compound of formula IV

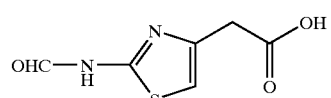

in and activated form to obtain a compound of formula I

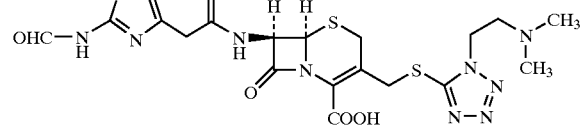

or a salt thereof and (ii) isolating said compound of formula I or a salt thereof.

9. A process which comprises 1) esterifying the carboxylic group in position 4 of the ring structure in a compound of formula I

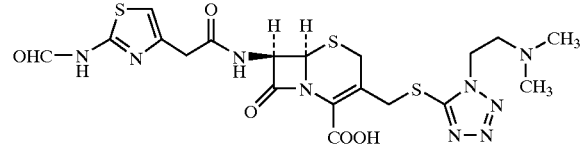

in free form or in salt form, to form N-formyl cefotiam hexetil; 2) deformylating said N-formyl cefotiam hexetil; and 3) isolating cefotiam hexetil.

* * * * *